United States Patent
Anderson et al.

(10) Patent No.: US 6,245,544 B1
(45) Date of Patent: Jun. 12, 2001

(54) HUMAN SERUM INDUCIBLE KINASE (SNK)

(75) Inventors: Karen M Anderson, West Chester, PA (US); Mark M Bouzyk, Little Hadham (GB); Michael J Hansbury, Collingswood, NJ (US); Jeffrey R Jackson, Collegeville, PA (US); Sandhya S Nerurkar, Devon, PA (US); Amy K Roshak, East Norriton, PA (US)

(73) Assignees: SmithKline Beecham Corporation, Philadelphia, PA (US); SmithKline Beecham plc, Middlesex (GB)

(*) Notice: Subject to any disclaimer, the term of this patent is extended or adjusted under 35 U.S.C. 154(b) by 0 days.

(21) Appl. No.: 09/505,744

(22) Filed: Feb. 16, 2000

Related U.S. Application Data

(62) Division of application No. 09/136,282, filed on Aug. 20, 1998, now Pat. No. 6,063,609.
(60) Provisional application No. 60/056,112, filed on Aug. 20, 1997.

(51) Int. Cl.[7] ............................... C12N 9/12; C07K 1/00
(52) U.S. Cl. .......................................... 435/194; 530/350
(58) Field of Search .............................. 435/194; 530/350

(56) References Cited

U.S. PATENT DOCUMENTS 5,885,803   3/1999   Bandman et al. .................. 435/69.1

OTHER PUBLICATIONS

Simmons et al. "Identification of an Early–Growth Response Gene Encoding a Novel Putative Protein Kinase", Molecular and Cellular Biology, vol. 12 (9), pp. 4164–4169 (1992).
Accession No. AF059617, Apr. 28, 1998.
Watanabe, et al. "Mutation of a single amino acid converts germ cell alkaline phasphatase to placental alkaline phosphatase", J. Biol. Chem., 1991, 266(31):21171–8 (Abstract).
Lee, et al., "An arginine to glutamine mutation in residue 109 of human ornithine transcarbamylase completely abolishes enzymatic activity in Cos1 cells", J. Clin Invest, 1989, 84(6):1762–6 (Abstract).
Chaidaroglou, et al., "Function of arginine–166 in the active site of *Escherichia coli* alkaline phosphatase", Biochemistry, 1988, 27(22):8338–43 (Abstract).
Simmons et al., Database pir64, Accession No. A44493, 1992.*
Bandman et al., database/geneseq 36, see the alignment, 1999.*

* cited by examiner

Primary Examiner—Rebecca E. Prouty
Assistant Examiner—M Monshipouri
(74) Attorney, Agent, or Firm—Elizabeth J. Hecht; Ratner & Prestia; William T. King

(57) ABSTRACT

The Serum Inducible Kinase (Snk) polypeptides and polynucleotides and methods for producing such polypeptides by recombinant techniques are disclosed. Also disclosed are methods for utilizing Serum Inducible Kinase (Snk) polypeptides and polynucleotides in therapy, and diagnostic assays for such.

2 Claims, No Drawings

HUMAN SERUM INDUCIBLE KINASE (SNK)

This application is a division of application Ser. No. 09/136,282, filed Aug. 20, 1998 now U.S. Pat. No. 6,063,609, which claims the benefit of U.S. Provisional Application No. 60/056,112, filed Aug. 20, 1997, both of whose contents are incorporated herein by reference in their entireties.

FIELD OF THE INVENTION

This invention relates to newly identified polypeptides and polynucleotides encoding such polypeptides, to their use in therapy and in identifying compounds which may be agonists, antagonists and/or inhibitors which are potentially useful in therapy, and to production of such polypeptides and polynucleotides.

BACKGROUND OF THE INVENTION

The drug discovery process is currently undergoing a fundamental revolution as it embraces 'functional genomics', that is, high throughput genome- or gene-based biology. This approach is rapidly superseding earlier approaches based on 'positional cloning'. A phenotype, that is a biological function or genetic disease, would be identified and this would then be tracked back to the responsible gene, based on its genetic map position.

Functional genomics relies heavily on the various tools of bioinformatics to identify gene sequences of potential interest from the many molecular biology databases now available. There is a continuing need to identify and characterise further genes and their related polypeptides/proteins, as targets for drug discovery.

Protein phosphorylation plays a critical role in promoting cell cycle progression. Most prominent among the regulators of the cell cycle is a family of cyclins, cyclin dependent kinases (CDKs), CDK regulatory kinases, and phosphatases (See Lees, E., Curr. Opin. Cell Biol. 1995, 7:773–780; Piwinica-Worms, H., J. Lab. Clin. Med. 1996, 128:350–354). A new family of cell cycle regulators, the polo-like kinases, has been identified and shown to be essential for progression through the cell cycle (Lane, H. A., Trends in Cell Biol. 1997, 7:63–68). This subfamily of serine/threonine kinases contains the following related but distinct members: (1) Plk (polo-like kinase; human) and its homologs Polo (Drosophila), cdc5 (*S. cerevisiae*), Plx (Xenopus), and Plo (*S. pombe*); (2) Prk (polo-related kinase; human) and its murine homolog Fnk; and (3) Snk (serum-inducible kinase; murine). Known functions of these genes include regulation of spindle assembly (human plk1, Drosophila polo, *S. pombe* plo1) and late nuclear division (*S. cerevisiae* cdc5). PLK1 expression correlates with the mitotic index (Holtrich U., Proc. Natl. Acad. Sci. 1994, 91:1736–1740) and mutations of the Drosophila polo or *S. cerevisiae* cdc5 gene cause mitotic arrest. In addition, antibodies directed against human PLK1 cause impaired mitosis. Progression from the G2 phase to the M phase of the cell cycle requires the activity of cdc25 phosphatase. PLX1 (Xenopus) phosphorylates and, thereby, activates cdc25-c, an isoform of cdc25 (Dunphy W. G., Science 1996. 273:1377–1380). The murine Snk is an early growth response gene which reportedly phosphorylates heterologous (although unidentified) substrates (Simmons D. L., Mol. Cell.Biol. 1992, 12:4164–4169). Identification of the consensus sequence of the polo-like family in the amino-terminal putative catalytic domain of Snk (published murine sequence and present invention) and the consensus polo box sequence in the carboxy terminus place this protein in the polo-like family and suggest that this enzyme is potentially a critical regulator of cell cycle progression.

SUMMARY OF THE INVENTION

The present invention relates to Serum Inducible Kinase (Snk), in particular Serum Inducible Kinase (Snk) polypeptides and Serum Inducible Kinase (Snk) polynucleotides, recombinant materials and methods for their production. In another aspect, the invention relates to methods for using such polypeptides and polynucleotides, including the treatment of proliferative diseases such as leukemia, solid tumor cancers and metastases; chronic inflammatory proliferative diseases such as psoriasis and rheumatoid arthritis; proliferative cardiovascular diseases such as restenosis; proliferative ocular disorders such as diabetic retinopathy; and benign hyperproliferative diseases such as hemangiomas, hereinafter referred to as "the Diseases", amongst others In a further aspect, the invention relates to methods for identifying agonists and antagonists/inhibitors using the materials provided by the invention, and treating conditions associated with Serum Inducible Kinase (Snk) imbalance with the identified compounds In a still further aspect, the invention relates to diagnostic assays for detecting diseases associated with inappropriate Serum Inducible Kinase (Snk) activity or levels.

DESCRIPTION OF THE INVENTION

In a first aspect, the present invention relates to Serum Inducible Kinase (Snk) polypeptides. Such peptides include isolated polypeptides comprising an amino acid sequence which has at least 70% identity, preferably at least 80% identity, more preferably at least 90% identity, yet more preferably at least 95% identity, most preferably at least 97–99% identity, to that of SEQ ID NO:2 over the entire length of SEQ ID NO:2. Such polypeptides include those comprising the amino acid of SEQ ID NO:2.

Further peptides of the present invention include isolated polypeptides in which the amino acid sequence has at least 70% identity, preferably at least 80% identity, more preferably at least 90% identity, yet more preferably at least 95% identity, most preferably at least 97–99% identity, to the amino acid sequence of SEQ ID NO:2 over the entire length of SEQ ID NO:2. Such polypeptides include the polypeptide of SEQ ID NO:2.

Further peptides of the present invention include isolated polypeptides encoded by a polynucleotide comprising the sequence contained in SEQ ID NO:1.

Polypeptides of the present invention are believed to be members of the Polo-like Kinase family of polypeptides. They are therefore of interest because the Polo-like Kinase family has an established, proven history as therapeutic targets. Clearly there is a need for identification and characterization of further members of the Polo-like Kinase family. These properties are hereinafter referred to as "Serum Inducible Kinase (Snk) activity" or "Serum Inducible Kinase (Snk) polypeptide activity" or "biological activity of Serum Inducible Kinase (Snk)". Also included amongst these activities are antigenic and immunogenic activities of said Serum Inducible Kinase (Snk) polypeptides, in particular the antigenic and immunogenic activities of the polypeptide of SEQ ID NO:2. Preferably, a polypeptide of the present invention exhibits at least one biological activity of Serum Inducible Kinase (Snk).

The polypeptides of the present invention may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

The present invention also includes include variants of the aforementioned polypeptides, that is polypeptides that vary from the referents by conservative amino acid substitutions, whereby a residue is substituted by another with like characteristics. Typical such substitutions are among Ala, Val, Leu and lie; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to Serum Inducible Kinase (Snk) polynucleotides. Such polynucleotides include isolated polynucleotides comprising a nucleotide sequence encoding a polypeptide which has at least 70% identity, preferably at least 80% identity, more preferably at least 90% identity, yet more preferably at least 95% identity, to the amino acid sequence of SEQ ID NO:2, over the entire length of SEQ ID NO:2. In this regard, polypeptides which have at least 97% identity are highly preferred, whilst those with at least 98–99% identity are more highly preferred, and those with at least 99% identity are most highly preferred. Such polynucleotides include a polynucleotide comprising the nucleotide sequence contained in SEQ ID NO:1 encoding the polypeptide of SEQ ID NO:2.

Further polynucleotides of the present invention include isolated polynucleotides comprising a nucleotide sequence that has at least 70% identity, preferably at least 80% identity, more preferably at least 90% identity, yet more preferably at least 95% identity,to a nucleotide sequence encoding a polypeptide of SEQ ID NO:2, over the entire coding region. In this regard, polynucleotides which have at least 97% identity are highly preferred, whilst those with at least 98–99% identity are more highly preferred, and those with at least 99% identity are most highly preferred.

Further polynucleotides of the present invention include isolated polynucleotides comprising a nucleotide sequence which has at least 70% identity, preferably at least 80% identity, more preferably at least 90% identity, yet more preferably at least 95% identity, to SEQ ID NO:1 over the entire length of SEQ ID NO:1. In this regard, polynucleotides which have at least 97% identity are highly preferred, whilst those with at least 98–99%identity are more highly preferred, and those with at least 99% identity are most highly preferred. Such polynucleotides include a polynucleotide comprising the polynucleotide of SEQ ID NO:1 as well as the polynucleotide of SEQ ID NO:1.

The invention also provides polynucleotides which are complementary to all the above described polynucleotides.

The nucleotide sequence of SEQ ID NO:1 shows homology with Murine Serum Inducible Kinase (Simmons et al., Mol. Cell. Biol. 12(9):4164–4169, 1992). The nucleotide sequence of SEQ ID NO:1 is a cDNA sequence and comprises a polypeptide encoding sequence (nucleotide 124 to 2181 encoding a polypeptide of 685 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The polypeptide of SEQ ID NO:2 is structurally related to other proteins of the Polo-like Kinase family, having homology and/or structural similarity with Murine Serum Inducible Kinase (Simmons et al., Mol. Cell. Biol. 12(9)4164–4169, 1992.

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one Serum Inducible Kinase (Snk) activity.

The present invention also relates to partial or other polynucleotide and polypeptide sequences which were first identified prior to the determination of the corresponding full length sequences of SEQ ID NO:1 and SEQ ID NO:2.

Accordingly, in a further aspect, the present invention provides for an isolated polynucleotide comprising:

(a) a nucleotide sequence which has at least 70% identity, preferably at least 80% identity, more preferably at least 90% identity, yet more preferably at least 95% identity, even more preferably at least 97–99% identity to SEQ ID NO:3 over the entire length of SEQ ID NO:3;

(b) a nucleotide sequence which has at least 70% identity, preferably at least 80% identity, more preferably at least 90% identity, yet more preferably at least 95% identity, even more preferably at least 97–99% identity, to SEQ ID NO:3 over the entire length of SEQ ID NO:3; or (c) the polynucleotide of SEQ ID NO:3.

The nucleotide sequence of SEQ ID NO:3 and the peptide sequence encoded thereby are derived from EST (Expressed Sequence Tag) sequences. It is recognized by those skilled in the art that there will inevitably be some nucleotide sequence reading errors in EST sequences (see Adams, M. D. et al, Nature 377 (supp) 3, 1995). Accordingly, the nucleotide sequence of SEQ ID NO:3 and the peptide sequence encoded therefrom are therefore subject to the same inherent limitations in sequence accuracy. Furthermore, the peptide sequence encoded by SEQ ID NO:3 comprises a region of identity or close homology and/or close structural similarity (for example a conservative amino acid difference) with the closest homologous or structurally similar protein.

Polynucleotides of the present invention may be obtained, using standard cloning and screening techniques, from a cDNA library derived from mRNA in cells of human H2LAS46, colon carcinoma, using the expressed sequence tag (EST) analysis (Adams, M. D., et al. Science (1991) 252:1651–1656; Adams, M. D. et al., Nature, (1992) 355:632–634; Adams, M. D., et al., Nature (1995) 377 Supp:3–174). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself; or the coding sequence for the mature polypeptide in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2 and in which several, for instance from 5 to 10, 1 to 5, 1 to 3, 1 to 2 or 1, amino acid residues are substituted, deleted or added, in any combination.

Polynucleotides which are identical or sufficiently identical to a nucleotide sequence contained in SEQ ID NO:1, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding homo logs and orthologs from species other than human) that have a high sequence similarity to SEQ ID NO:1. Typically these nucleotide sequences are 70% identical, preferably 80% identical, more preferably 90% identical, most preferably 95% identical to that of the referent. The probes or primers will generally comprise at least 15 nucleotides, preferably, at least 30 nucleotides and may have at least 50 nucleotides. Particularly preferred probes will have between 30 and 50 nucleotides.

A polynucleotide encoding a polypeptide of the present invention, including homologs and orthologs from species other than human, may be obtained by a process which comprises the steps of screening an appropriate library under stringent hybridization conditions with a labeled probe having the sequence of SEQ ID NO: 1 or a fragment thereof, and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at about 65° C. Thus the present invention also includes polynucleotides obtainable by screening an appropriate library under stringent hybridization conditions with a labeled probe having the sequence of SEQ ID NO:1 or a fragment thereof.

The skilled artisan will appreciate that, in many cases, an isolated cDNA sequence will be incomplete, in that the region coding for the polypeptide is cut short at the 5' end of the cDNA. This is a consequence of reverse transcriptase, an enzyme with inherently low 'processivity' (a measure of the ability of the enzyme to remain attached to the template during the polymerisation reaction), failing to complete a DNA copy of the mRNA template during 1st strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998–9002, 1988). Recent modifications of the technique, exemplified by the Marathon™' technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

This invention also relates to the use of polynucleotides of the present invention as diagnostic reagents. Detection of a mutated form of the gene characterized by the polynucleotide of SEQ ID NO:1 which is associated with a dysfunction will provide a diagnostic tool that can add to, or define, a diagnosis of a disease, or susceptibility to a disease, which results from under-expression, over-expression or altered expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled Serum Inducible Kinase (Snk) nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (e.g., Myers et al., *Science* (1985) 230:1242). Sequence changes at specific locations may also be revealed by nuclease protection assays, such as RNase and S1 protection or the chemical cleavage method (see Cotton et al., *Proc Natl Acad Sci USA* (1985) 85: 4397–4401). In another embodiment, an array of oligonucleotides probes comprising Serum Inducible Kinase (Snk) nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, Vol 274, pp 610–613 (1996)).

The diagnostic assays offer a process for diagnosing or determining a susceptibility to the Diseases through detection of mutation in the Serum Inducible Kinase (Snk) gene by the methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagnostic kit which comprises:

(a) a polynucleotide of the present invention, preferably the nucleotide sequence of SEQ ID NO:1, or a fragment thereof;

(b) a nucleotide sequence complementary to that of (a);

(c) a polypeptide of the present invention, preferably the polypeptide of SEQ ID NO:2 or a fragment thereof; or (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a disease, particularly proliferative diseases such as leukemia, solid tumor cancers and metastases; chronic inflammatory proliferative diseases such as psoriasis and rheumatoid arthritis; proliferative cardiovascular diseases such as restenosis; proliferative ocular disorders such as diabetic retinopathy; and benign hyperproliferative diseases such as hemangiomas, amongst others.

The nucleotide sequences of the present invention are also valuable for chromosome identification. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease. The gene of the present invention maps to human chromosome5d12.1-q13.2/D5S491–D5S427.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

Antibodies against polypeptides of the present invention may also be employed to treat the Diseases, amongst others.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Another aspect of the invention relates to a method for inducing an immunological response in a mammal which comprises inoculating the mammal with a polypeptide of the present invention, adequate to produce antibody and/or T cell immune response to protect said animal from the Diseases hereinbefore mentioned amongst others. Yet another aspect of the invention relates to a method of inducing immunological response in a mammal which comprises, delivering a polypeptide of the present invention via a vector directing expression of the polynucleotide and coding for the polypeptide in vivo in order to induce such an immunological response to produce antibody to protect said animal from diseases.

A further aspect of the invention relates to an immunological/vaccine formulation (composition) which, when introduced into a mammalian host, induces an immunological response in that mammal to a polypeptide of the present invention wherein the composition comprises a polypeptide or polynucleotide of the present invention. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention are responsible for many biological functions, including many disease states, in particular the Diseases hereinbefore mentioned. It is therefore desirous to devise screening methods to identify compounds which stimulate or which inhibit the function of the polypeptide. Accordingly, in a further aspect, the present invention provides for a method of screening compounds to identify those which stimulate or which inhibit the function of the polypeptide. In general, agonists or antagonists may be employed for therapeutic and prophylactic purposes for such Diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of the polypeptide; or may be structural or functional mimetics thereof (see Coligan et al., Current Protocols in Immunology 1(2):Chapter5 (1991)).

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Constitutively active polypeptides may be employed in screening methods for inverse agonists or inhibitors, in the absence of an agonist or inhibitor, by testing whether the candidate compound results in inhibition of activation of the polypeptide. Further, the screening methods may simply comprise the steps of mixing a candidate compound with a solution containing a polypeptide of the present invention, to form a mixture, measuring Serum Inducible Kinase (Snk) activity in the mixture, and comparing the Serum Inducible Kinase (Snk) activity of the mixture to a standard. Fusion proteins, such as those made from Fc portion and Serum Inducible Kinase (Snk) polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide(also called antagonist or agonist, respectively) from suitably manipulated cells or tissues.

The polypeptide may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide which compete with the binding of the polypeptide to its receptors, if any. Standard methods for conducting such assays are well understood in the art.

Examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Thus, in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:
(a) a polypeptide of the present invention;
(b) a recombinant cell expressing a polypeptide of the present invention;
(c) a cell membrane expressing a polypeptide of the present invention; or
(d) antibody to a polypeptide of the present invention;
which polypeptide is preferably that of SEQ ID NO:2.

It will be appreciated that in any such kit, (a), (b), (c) or (d) may comprise a substantial component.

It will be readily appreciated by the skilled artisan that a polypeptide of the present invention may also be used in a method for the structure-based design of an agonist, antagonist or inhibitor of the polypeptide, by:
(a) determining in the first instance the three-dimensional structure of the polypeptide;
(b) deducing the three-dimensional structure for the likely reactive or binding site(s) of an agonist, antagonist or inhibitor;
(c) synthesizing candidate compounds that are predicted to bind to or react with the deduced binding or reactive site; and
(d) testing whether the candidate compounds are indeed agonists, antagonists or inhibitors.

It will be further appreciated that this will normally be an interactive process.

In a further aspect, the present invention provides methods of treating abnormal conditions such as, for instance, proliferative diseases such as leukemia, solid tumor cancers and metastases; chronic inflammatory proliferative diseases such as psoriasis and rheumatoid arthritis; proliferative cardiovascular diseases such as restenosis; proliferative ocular disorders such as diabetic retinopathy; and benign hyperproliferative diseases such as hemangiomas, related to either an excess of, or an under-expression of, Serum Inducible Kinase (Snk) polypeptide activity.

If the activity of the polypeptide is in excess, several approaches are available. One approach comprises administering to a subject in need thereof an inhibitor compound (antagonist) as hereinabove described, optionally in combination with a pharmaceutically acceptable carrier, in an amount effective to inhibit the function of the polypeptide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide may be administered. Typical examples of such competitors include fragments of the Serum Inducible Kinase (Snk) polypeptide.

In still another approach, expression of the gene encoding endogenous Serum Inducible Kinase (Snk) polypeptide can be inhibited using expression blocking techniques. Known such techniques involve the use of antisense sequences, either internally generated or separately administered (see, for example, O'Connor, *J Neurochem* (1991) 56:560 in Oligodeoxynucleotides as Antisense Inhibitors of Gene Expression, CRC Press, Boca Raton, Fla. (1988)). Alternatively, oligonucleotides which form triple helices with the gene can be supplied (see, for example, Lee et al., *Nucleic Acids Res* (1979) 6:3073; Cooney et al., *Science* (1988) 241:456; Dervan et al., *Science* (1991) 251:1360). These oligomers can be administered per se or the relevant oligomers can be expressed in vivo.

For treating abnormal conditions related to an under-expression of Serum Inducible Kinase (Snk) and its activity, several approaches are also available. One approach comprises administering to a subject a therapeutically effective amount of a compound which activates a polypeptide of the present invention, i.e., an agonist as described above, in combination with a pharmaceutically acceptable carrier, to thereby alleviate the abnormal condition. Alternatively, gene therapy may be employed to effect the endogenous production of Serum Inducible Kinase (Snk) by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of a polypeptide of the present invention in combination with a suitable pharmaceutical carrier.

In a further aspect, the present invention provides for pharmaceutical compositions comprising a therapeutically effective amount of a polypeptide, such as the soluble form of a polypeptide of the present invention, agonist/antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

The dosage range required depends on the choice of peptide or other compounds of the present invention, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Polynucleotide and polypeptide sequences form a valuable information resource with which to identify further sequences of similar homology. This is most easily facilitated by storing the sequence in a computer readable medium and then using the stored data to search a sequence database using well known searching tools, such as GCC. Accordingly, in a further aspect, the present invention provides for a computer readable medium having stored thereon a polynucleotide comprising the sequence of SEQ ID NO:1 and/or a polypeptide sequence encoded thereby.

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"solated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, PROTEINS-STRUCTURE AND MOLECULAR PROPERTIES, 2nd Ed., T. E. Creighton, W. H. Freeman and Company, New York, 1993; Wold, F., Post-translational Protein Modifications: Perspectives and Prospects, pgs. 1–12 in POST-TRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Post-translational Modifications and Aging", *Ann NY Acad Sci* (1992) 663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., *SIAM J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Parameters for polypeptide sequence comparison include the following:
1) Algorithm: Needleman and Wunsch, J. Mol Biol. 48: 443–453 (1970)
Comparison matrix: BLOSSUM62 from Hentikoff and Hentikoff, Proc. Natl. Acad. Sci. USA. 89:10915–10919 (1992)
Gap Penalty: 12
Gap Length Penalty: 4
A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:
1) Algorithm: Needleman and Wunsch, J. Mol Biol. 48: 443–453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO:1, wherein said polynucleotide sequence may be identical to the reference sequence of SEQ ID NO: 1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of amino acids in SEQ ID NO:2 by the integer defining the percent identity divided by 100 and then subtracting that product from said total number of amino acids in SEQ ID NO:2, or:

$$n_n \leq x_n - (x_n \cdot y),$$

wherein $n_n$ is the number of amino acid alterations, $x_n$ is the total number of amino acids in SEQ ID NO:2, y is, for instance 0.70 for 70%. 0.80 for 80%, 0.85 for 85% etc., · is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said polypeptide sequence may be identical to the reference sequence of SEQ ID NO: 2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is, for instance 0.70 for 70%, 0.80 for 80%, 0.85 for 85% etc., and · is the symbol for the multiplication operator, and wherein any non-integer product of $x_a$ and y is rounded down to the nearest integer prior to subtracting it from $x_a$.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

All publications, including but not limited to patents and patent applications, cited in this specification are herein incorporated by reference as if each individual publication were specifically and individually indicated to be incorporated by reference herein as though fully set forth.

What is claimed is:

1. An isolated polypeptide comprising the amino acid sequence of SEQ ID NO:2.

2. An isolated polypeptide consisting of the amino acid sequence of SEQ ID NO: 2.

* * * * *

SEQUENCE LISTING

```
<160> NUMBER OF SEQ ID NOS: 3

<210> SEQ ID NO: 1
<211> LENGTH: 2783
<212> TYPE: DNA
<213> ORGANISM: HOMO SAPIENS
<220> FEATURE:
<221> NAME/KEY: UNSURE
<222> LOCATION: (2720)(2721)

<400> SEQUENCE: 1
```

-continued

| | | | |
|---|---|---|---|
| ggcacgaggt | tgggtgctat | tcggcaccag | aggcaagggt gcgaggacca cggccggctc | 60 |
| ggacgtgtga | ccgcgcctag | ggggtggcag | cgggcagtgc ggggcggcaa ggcgaccatg | 120 |
| gagcttttgc | ggactatcac | ctaccagcca | gccgccagca ccaaaatgtg cgagcaggcg | 180 |
| ctgggcaagg | gttgcggagc | agactcgaag | aagaagcggc cgccgcagcc ccccgaggaa | 240 |
| tcgcagccac | ctcagtccca | ggcgcaagtg | ccccgcgg cccctcacca ccatcaccac | 300 |
| cattcgcact | cggggccgga | gatctcgcgg | attatcgtcg accccacgac tgggaagcgc | 360 |
| tactgccggg | gcaaagtgct | gggaaagggt | ggctttgcaa aatgttacga gatgacagat | 420 |
| ttgacaaata | acaaagtcta | cgccgcaaaa | attattcctc acagcagagt agctaaacct | 480 |
| catcaaaggg | aaaagattga | caaagaaata | gagcttcaca gaattcttca tcataagcat | 540 |
| gtagtgcagt | tttaccacta | cttcgaggac | aaagaaaaca tttacattct cttggaatac | 600 |
| tgcagtagaa | ggcaatggct | catatttga | agcaagaaa ggtgttgaca gagccagaag | 660 |
| ttcgatacta | cctcaggcag | attgtgtctg | gactgaaata ccttcatgaa caagaaatct | 720 |
| tgcacagaga | tctcaaacta | gggaactttt | ttattaatga agccatggaa ctaaaagttg | 780 |
| gggacttcgg | tctggcagcc | aggctagaac | ccttggaaca cagaaggaga acgatatgtg | 840 |
| gtaccccaaa | ttatctctct | cctgaagtcc | tcaacaaaca aggacatggc tgtgaatcag | 900 |
| acatttgggc | cctgggctgt | gtaatgtata | caatgttact agggaggccc ccatttgaaa | 960 |
| ctacaaatct | caaagaaact | tataggtgca | taagggaagc aaggtataca atgccgtcct | 1020 |
| cattgctggc | tcctgccaag | cacttaattg | ctagtatgtt gtccaaaaac ccagaggata | 1080 |
| ggcctagttt | ggatgacatc | attcgacatg | acttttttt gcagggcttc actccggaca | 1140 |
| gactgtcttc | tagctgttgt | catacagttc | cagatttcca cttatcaagc ccagctaaga | 1200 |
| atttctttaa | gaaagcagct | gctgctcttt | ttggtggcaa aaaagacaaa gcaagatata | 1260 |
| ttgacacaca | taatagagtg | tctaaagaag | atgaagacat ctacaagctt aggcatgatt | 1320 |
| tgaaaaagac | ttcaataact | cagcaaccca | gcaaacacag gacagatgag gagctccagc | 1380 |
| cacctaccac | cacagttgcc | aggtctggaa | caccccgcagt agaaaacaag cagcagattg | 1440 |
| gggatgctat | tcggatgata | gtcagaggga | ctcttggcag ctgtagcagc agcagtgaat | 1500 |
| gccttgaaga | cagtaccatg | ggaagtgttg | cagacacagt ggcaagggtt cttcggggat | 1560 |
| gtctggaaaa | catgccggaa | gctgattgca | ttcccaaaga gcagctgagc acatcatttc | 1620 |
| agtgggtcac | caaatgggtt | gattactcta | acaaatatgg ctttgggtac cagctctcag | 1680 |
| accacaccgt | cggtgtcctt | ttcaacaatg | tgctcacat gagcctcctt ccagacaaaa | 1740 |
| aaacagttca | ctattacgca | gagcttggcc | aatgctcagt tttcccagca acagatgctc | 1800 |
| ctgagcaatt | tattagtcaa | gtgacggtgc | tgaaatactt ttctcattac atggaggaga | 1860 |
| acctcatgga | tggtggagat | ctgcctagtg | ttactgatat tcgaagacct cggctctacc | 1920 |
| tccttcagtg | gctaaaatct | gataaggccc | taatgatgct ctttaatgat ggcacctttc | 1980 |
| aggtgaattt | ctaccatgat | catacaaaaa | tcatcatctg tagccaaaat gaagaatacc | 2040 |
| ttctcaccta | catcaatgag | gataggatat | ctacaacttt caggctgaca actctgctga | 2100 |
| tgtctggctg | ttcatcagaa | ttaaaaaatc | gaatggaata tgccctgaac atgctcttac | 2160 |
| aaagatgtaa | ctgaaagact | tttcgaatgg | accctatggg actcctcttt tccactgtga | 2220 |
| gatctacagg | gaacccaaaa | gaatgatcta | gagtatgttg aagaagatgg acatgtggtg | 2280 |
| gtacgaaaac | aattcccctg | tggcctgctg | gactgggtga accagaaca ggctaaggca | 2340 |
| tacagttctt | gactttggac | aatccaagag | tgaaccagaa tgcagttttc cttgagatac | 2400 |

-continued

```
ctgtttttaaa aggtttttca gacaattttg cagaaaggtg cattgattct taaattctct    2460
ctgttgagag catttcagcc agaggacttt ggaactgtga atatacttcc tgaaggggag    2520
ggagaaggga ggaagctccc atgttgttta aaggctgtaa ttggagcagc ttttggctgc    2580
gtaactgtga actatggcca tatataattt tttttcatta attttttgaag atacttgtgg    2640 ctggaaaagt gcattccttg ttaataaact ttttatttat tacagcccaa agagcagtat    2700
ttattatcaa aatgtctttn nctttgacca ttttaaaccg ttggcaataa agagtatgaa    2760
aacgcaaaaa aaaaaaaaaa aaa                                            2783
```

<210> SEQ ID NO: 2
<211> LENGTH: 685
<212> TYPE: PRT
<213> ORGANISM: HOMO SAPIENS

<400> SEQUENCE: 2

```
Met Glu Leu Leu Arg Thr Ile Thr Tyr Gln Pro Ala Ala Ser Thr Lys
 1               5                  10                  15

Met Cys Glu Gln Ala Leu Gly Lys Gly Cys Gly Ala Asp Ser Lys Lys
            20                  25                  30

Lys Arg Pro Pro Gln Pro Pro Glu Glu Ser Gln Pro Pro Gln Ser Gln
        35                  40                  45

Ala Gln Val Pro Pro Ala Ala Pro His His His His His Ser His
    50                  55                  60

Ser Gly Pro Glu Ile Ser Arg Ile Ile Val Asp Pro Thr Thr Gly Lys
65                  70                  75                  80

Arg Tyr Cys Arg Gly Lys Val Leu Gly Lys Gly Phe Ala Lys Cys
                85                  90                  95

Tyr Glu Met Thr Asp Leu Thr Asn Asn Lys Val Tyr Ala Ala Lys Ile
            100                 105                 110

Ile Pro His Ser Arg Val Ala Lys Pro His Gln Arg Glu Lys Ile Asp
        115                 120                 125

Lys Glu Ile Glu Leu His Arg Ile Leu His His Lys His Val Val Gln
    130                 135                 140

Phe Tyr His Tyr Phe Glu Asp Lys Glu Asn Ile Tyr Ile Leu Leu Glu
145                 150                 155                 160

Tyr Cys Ser Arg Arg Ser Met Ala His Ile Leu Lys Ala Arg Lys Val
                165                 170                 175

Leu Thr Glu Pro Glu Val Arg Tyr Tyr Leu Arg Gln Ile Val Ser Gly
            180                 185                 190

Leu Lys Tyr Leu His Glu Gln Glu Ile Leu His Arg Asp Leu Lys Leu
        195                 200                 205

Gly Asn Phe Phe Ile Asn Glu Ala Met Glu Leu Lys Val Gly Asp Phe
    210                 215                 220

Gly Leu Ala Ala Arg Leu Glu Pro Leu Glu His Arg Arg Thr Ile
225                 230                 235                 240

Cys Gly Thr Pro Asn Tyr Leu Ser Pro Glu Val Leu Asn Lys Gln Gly
                245                 250                 255

His Gly Cys Glu Ser Asp Ile Trp Ala Leu Gly Cys Val Met Tyr Thr
            260                 265                 270

Met Leu Leu Gly Arg Pro Pro Phe Glu Thr Thr Asn Leu Lys Glu Thr
        275                 280                 285

Tyr Arg Cys Ile Arg Glu Ala Arg Tyr Thr Met Pro Ser Ser Leu Leu
    290                 295                 300
```

```
Ala Pro Ala Lys His Leu Ile Ala Ser Met Leu Ser Lys Asn Pro Glu
305                 310                 315                 320

Asp Arg Pro Ser Leu Asp Asp Ile Ile Arg His Asp Phe Phe Leu Gln
            325                 330                 335

Gly Phe Thr Pro Asp Arg Leu Ser Ser Cys Cys His Thr Val Pro
            340                 345                 350

Asp Phe His Leu Ser Ser Pro Ala Lys Asn Phe Phe Lys Lys Ala Ala
            355                 360                 365

Ala Ala Leu Phe Gly Gly Lys Lys Asp Lys Ala Arg Tyr Ile Asp Thr
370                 375                 380

His Asn Arg Val Ser Lys Glu Asp Glu Asp Ile Tyr Lys Leu Arg His
385                 390                 395                 400

Asp Leu Lys Lys Thr Ser Ile Thr Gln Gln Pro Ser Lys His Arg Thr
                405                 410                 415

Asp Glu Glu Leu Gln Pro Pro Thr Thr Val Ala Arg Ser Gly Thr
                420                 425                 430

Pro Ala Val Glu Asn Lys Gln Gln Ile Gly Asp Ala Ile Arg Met Ile
            435                 440                 445

Val Arg Gly Thr Leu Gly Ser Cys Ser Ser Ser Glu Cys Leu Glu
450                 455                 460

Asp Ser Thr Met Gly Ser Val Ala Asp Thr Val Ala Arg Val Leu Arg
465                 470                 475                 480

Gly Cys Leu Glu Asn Met Pro Glu Ala Asp Cys Ile Pro Lys Glu Gln
                485                 490                 495

Leu Ser Thr Ser Phe Gln Trp Val Thr Lys Trp Val Asp Tyr Ser Asn
                500                 505                 510

Lys Tyr Gly Phe Gly Tyr Gln Leu Ser Asp His Thr Val Gly Val Leu
            515                 520                 525

Phe Asn Asn Gly Ala His Met Ser Leu Leu Pro Asp Lys Lys Thr Val
530                 535                 540

His Tyr Tyr Ala Glu Leu Gly Gln Cys Ser Val Phe Pro Ala Thr Asp
545                 550                 555                 560

Ala Pro Glu Gln Phe Ile Ser Gln Val Thr Val Leu Lys Tyr Phe Ser
                565                 570                 575

His Tyr Met Glu Glu Asn Leu Met Asp Gly Gly Asp Leu Pro Ser Val
            580                 585                 590

Thr Asp Ile Arg Arg Pro Arg Leu Tyr Leu Leu Gln Trp Leu Lys Ser
            595                 600                 605

Asp Lys Ala Leu Met Met Leu Phe Asn Asp Gly Thr Phe Gln Val Asn
610                 615                 620

Phe Tyr His Asp His Thr Lys Ile Ile Ile Cys Ser Gln Asn Glu Glu
625                 630                 635                 640

Tyr Leu Leu Thr Tyr Ile Asn Glu Asp Arg Ile Ser Thr Thr Phe Arg
                645                 650                 655

Leu Thr Thr Leu Leu Met Ser Gly Cys Ser Ser Glu Leu Lys Asn Arg
            660                 665                 670

Met Glu Tyr Ala Leu Asn Met Leu Leu Gln Arg Cys Asn
            675                 680                 685

<210> SEQ ID NO: 3
<211> LENGTH: 2789
<212> TYPE: DNA
<213> ORGANISM: HOMO SAPIENS
```

<400> SEQUENCE: 3

```
ggcacgaggt tgggtgctat tcggcaccag aggcaagggt gcgaggacca cggccggctc      60
ggacgtgtga ccgcgcctag ggggtggcag cgggcagtgc ggggcggcaa ggcgaccatg     120
gagcttttgc ggactatcac ctaccagcca gccgccagca ccaaaatgtg cgagcaggcg     180
ctgggcaagg gttgcggagc agactcgaag aagaagcggc cgccgcagcc ccccgaggaa     240
tcgcagccac ctcagtccca ggcgcaagtg cccccggcgg ccctcacca ccatcaccac      300
cattcgcact cggggccgga gatctcgcgg attatcgtcg accccacgac tgggaagcgc     360
tactgccggg gcaaagtgct gggaaagggt ggctttgcaa aatgttacga gatgacagat     420
ttgacaaata caaagtctca cgccgcaaaa attattcctc acagcagagt agctaaacct     480
catcaaaggg aaaagattga caaagaaata gagcttcaca gaattcttca tcataagcat     540
gtagtgcagt tttaccacta cttcgaggac aaagaaaaca tttacattct cttggaatac     600
tgcagtagaa ggtcaatggc tcatattttg aaagcaagaa aggtgttgac agagccagaa     660
gttcgatact acctcaggca gattgtgtct ggactgaaat accttcatga caagaaatc      720
ttgcacagag atctcaaact agggaacttt tttattaatg aagccatgga actaaaagtt     780
ggggacttcg gtctggcagc caggctagaa cccttggaac acagaaggag aacgatatgt     840
ggtaccccaa attatctctc tcctgaagtc ctcaacaaac aaggacatgg ctgtgaatca     900
gacatttggg ccctgggctg tgtaatgtat acaatgttac tagggaggcc cccatttgaa     960
actacaaatc tcaaagaaac ttataggtgc ataagggaag caagtatac aatgccgtcc     1020
tcattgctgg ctcctgccaa gcacttaatt gctagtatgt tgtccaaaaa cccagaggat    1080
cgtcccagtt tggatgacat cattcgacat gactttttt tgcagggctt cactccggac    1140
agactgtctt ctagctgttg tcatacagtt ccagatttcc acttatcaag cccagctaag    1200
aatttcttta agaaagcagc tgctgctctt tttggtggca aaaaagacaa agcaagatat    1260
attgacacac ataatagagt gtctaaagaa gatgaagaca tctacaagct taggcatgat    1320
ttgaaaaaga cttcaataac tcagcaaccc agcaaacaca ggacagatga ggagctccag    1380
ccacctacca ccacagttgc caggtctgga acacccgcag tagaaaacaa gcagcagatt    1440
ggggatgcta ttcggatgat agtcagaggg actcttggca gctgtagcag cagcagtgaa    1500
tgccttgaag acagtaccat gggaagtgtt gcagacacag tggcaagggt tcttcgggga    1560
tgtctggaaa catgccggga agctgattgc attcccaaag agcagctgag cacatcattt    1620
cagtgggtca ccaaatgggt tgattactct aacaaatatg gctttgggta ccagctctca    1680
gaccacaccg tcggtgtcct tttcaacaat ggtgctcaca tgagcctcct tccagacaaa    1740
aaaacagttc actattacgc agagcttggc caatgctcag ttttcccagc aacagatgct    1800
cctgagcaat ttattagtca agtgacggtg ctgaaatact tttctcatta catggaggag    1860
aacctcatgg atggtggaga tctgcctagt gttactgata ttcgaagacc tcggctctac    1920
ctccttcagt ggctaaaatc tgataaggcc ctaatgatgc tctttaatga tggcaccttt    1980
caggtgaatt ctaccatga tcatacaaaa atcatcatct gtagccaaaa tgaagaatac    2040
cttctcacct acatcaatga ggataggata tctacaactt tcaggctgac aactctgctg    2100
atgtctggct gttcatcaga attaaaaaat cgaatggaat atgccctgaa catgctctta    2160
caaagatgta actgaaagac ttttcgaatg gacccatatgg gactcctctt ttccactgtg    2220
agatctacag ggaacccaaa agaatgatct agagtatgtt gaagagatgg acatgtggt    2280
ggtacgaaaa caattcccct gtggcctgct ggactgggtg gaaccagaac aggctaaggc    2340
```

```
atacagttct tgactttgga caatccaaga gtgaaccaga atgcagtttt ccttgagata    2400
cctgttttaa aaggtttttc agacaatttt gcagaaaggt gcattgattc ttaaattctc    2460
tctgttgaga gcatttcagc cagaggactt tggaactgtg aatatacttc ctgaagggga    2520
gggagaaggg aggaagctcc catgttgttt aaaggctgta attggagcag cttttggctg    2580
cgtaactgtg aactatggcc atatataatt tttttcatt  aattttgaa  gatacttgtg    2640 gctggaaaag tgcattcctt gttaataaac ttttattta  ttacagccca aagagcagta    2700
tttattatca aaatgtcttt tttttatgt  tgaccatttt aaaccgttgg caataaagag    2760
tatgaaaacg caaaaaaaaa aaaaaaaa                                       2789
```